US00PP14887P2

(12) United States Plant Patent
Scholten

(10) Patent No.: US PP14,887 P2
(45) Date of Patent: Jun. 8, 2004

(54) CITRUS PLANT NAMED 'MOSQUITO'

(50) Latin Name: *Citrus aurantifolius*
Varietal Denomination: Mosquito

(75) Inventor: Dirck Scholten, Boskoop (NL)

(73) Assignee: Witteman + Co., Hillegom (NL)

( * ) Notice: Subject to any disclaimer, the term of this patent is extended or adjusted under 35 U.S.C. 154(b) by 0 days.

(21) Appl. No.: 10/437,946

(22) Filed: May 13, 2003

(51) Int. Cl.[7] ..... A01H 5/00
(52) U.S. Cl. ..... Plt./201
(58) Field of Search ..... Plt./201

(56) References Cited

PUBLICATIONS

UPOV ROM GTITM Computer Database, GTI JOUVE Retrieval software 2003/05 citation for 'Mosquito'.*

* cited by examiner

*Primary Examiner*—Bruce R. Campell
*Assistant Examiner*—W C Haas
(74) *Attorney, Agent, or Firm*—C. A. Whealy

(57) ABSTRACT

A distinct cultivar of Citrus plant named 'Mosquito', characterized by its upright and rounded plant form; freely branching growth habit; dark red-colored developing leaves; and green and yellow variegated fully expanded leaves.

2 Drawing Sheets

Botanical classification/cultivar designation: *Citrus aurantifolius* cultivar Mosquito

BACKGROUND OF THE INVENTION

The present Invention relates to a new and distinct cultivar of Citrus plant, botanically known as *Citrus aurantifolius,* commercially known as Lime, and hereinafter referred to by the name 'Mosquito'.

The new Citrus was discovered by the Inventor in 1985 in a controlled environment in Boskoop, The Netherlands, as a naturally-occurring whole plant mutation of an unidentified selection of *Citrus aurantifolius,* not patented. The new Citrus was selected by the Inventor on the basis of its unique dark red-colored developing leaves and green and yellow variegated fully expanded leaves.

Asexual reproduction of the new Citrus by cuttings in a controlled environment in Boskoop, The Netherlands, since 1987, has shown that the unique features of this new Citrus are stable and reproduced true to type in successive generations.

SUMMARY OF THE INVENTION

Plants of the cultivar Mosquito have not been observed under all possible environmental conditions. The phenotype may vary somewhat with variations in environment such as temperature and light intensity without, however, any variance in genotype.

The following traits have been repeatedly observed and are determined to be the unique characteristics of 'Mosquito'. These characteristics in combination distinguish 'Mosquito' as a new and distinct cultivar:

1. Upright and rounded plant form.
2. Freely branching growth habit.
3. Dark red-colored developing leaves.
4. Green and yellow variegated fully expanded leaves.

Plants of the cultivar Mosquito differ from the parent selection and other Lime cultivars known to the Inventor in its unique dark red-colored developing leaves.

BRIEF DESCRIPTION OF THE PHOTOGRAPHS

The accompanying colored photographs illustrate the overall appearance of the new Citrus, showing the colors as true as it is reasonably possible to obtain in colored reproductions of this type. Colors in the photographs may differ slightly from the color values cited in the detailed botanical description which accurately describe the colors of the new Citrus.

The photograph on the first sheet comprises a side perspective view of a typical plant of 'Mosquito' grown in a container. The photograph at the top of the second sheet is a close-up view of typical developing leaves of 'Mosquito'. The photograph at the bottom of the second sheet is a close-up view of the upper surface of a typical fully expanded leaf of 'Mosquito'.

DETAILED BOTANICAL DESCRIPTION

In the following description, color references are made to The Royal Horticultural Society Colour Chart, 2001 Edition, except where general terms of ordinary dictionary significance are used. Plants used for the photographs and the following description were about two years old and grown under outdoor field conditions which closely approximate commercial production conditions in Boskoop, The Netherlands. During the production of the plants, day temperatures ranged from 8 to 16° C. and night temperatures ranged from 2 to 8° C. The photographs and description were taken in November, 2002.

Botanical classification: *Citrus aurantifolius* cultivar Mosquito.

Parentage: Naturally-occurring whole plant mutation of an unidentified selection of *Citrus aurantifolius,* not patented.

Propagation:

*Type.*—By softwood cuttings.

*Time to initiate roots.*—About 35 days at 25° C.

*Time to produce a rooted cutting.*—About 120 days at 20° C.

*Root description.*—Fine, fibrous.

Plant description:

*Form.*—Evergreen shrub; upright, somewhat outwardly spreading and rounded plant form; moderately vigorous growth habit.

*Plant height.*—About 32 cm.

*Plant diameter.*—About 30 cm.

*Lateral branches.*—Quantity: About eight per plant; pinching enhances branching. Fragrance: Pleasant lime fragrance when rubbed or crushed.

*Length.*—About 10.3 cm.

*Diameter.*—About 3.5 mm.

*Internode length.*—About 1.8 cm.

*Strength.*—Strong.

*Texture.*—Smooth.

*Color.*—144D to 145A.

*Thorns.*—Single thorns occasionally observed at a developing axillary branch. Length: About 3 mm. Width, at base: About 1 mm. Shape: Roughly lanceolate. Texture: Smooth. Color: 144D to 145A.

*Foliage description.*—Arrangement: Alternate, simple. Fragrance: Pleasant lemon fragrance when rubbed or crushed. Length: About 7.4 cm. Width: About 3.4 cm. Shape: Elliptic to narrowly ovate.

*Apex.*—Acute to apiculate.

*Base.*—Acuminate.

*Margin.*—Shallowly serrated.

*Texture, upper and lower surfaces.*—Leathery; smooth, glabrous.

*Venation pattern.*—Pinnate.

*Color.*—Developing foliage, upper surface: More red than 200A to 200B. Developing foliage, lower surface: N199A to 148A to 148B. Fully expanded foliage, upper surface: Irregularly shaped centers, 137A, with random irregularly shaped areas, 137C to 138A; towards the margin, 8A to 8B to 10A. Fully expanded foliage, lower surface: Irregularly shaped centers, 138B; towards the margin, 11B to 160A to 160B. Venation, upper surface: Midrib, 147C to 147D; lateral veins same as lamina. Venation, lower surface: Midrib, 144D; lateral veins same as lamina.

*Petiole.*—Length: About 6 mm. Diameter: About 2 mm. Texture: Smooth. Color: 144C.

Flower description: Flower development has not been observed.

Disease/pest resistance: Plants of the new Citrus have not been noted to be resistant to pathogens and pests common to Citrus.

It is claimed:

1. A new and distinct cultivar of Citrus plant named 'Mosquito', as illustrated and described.

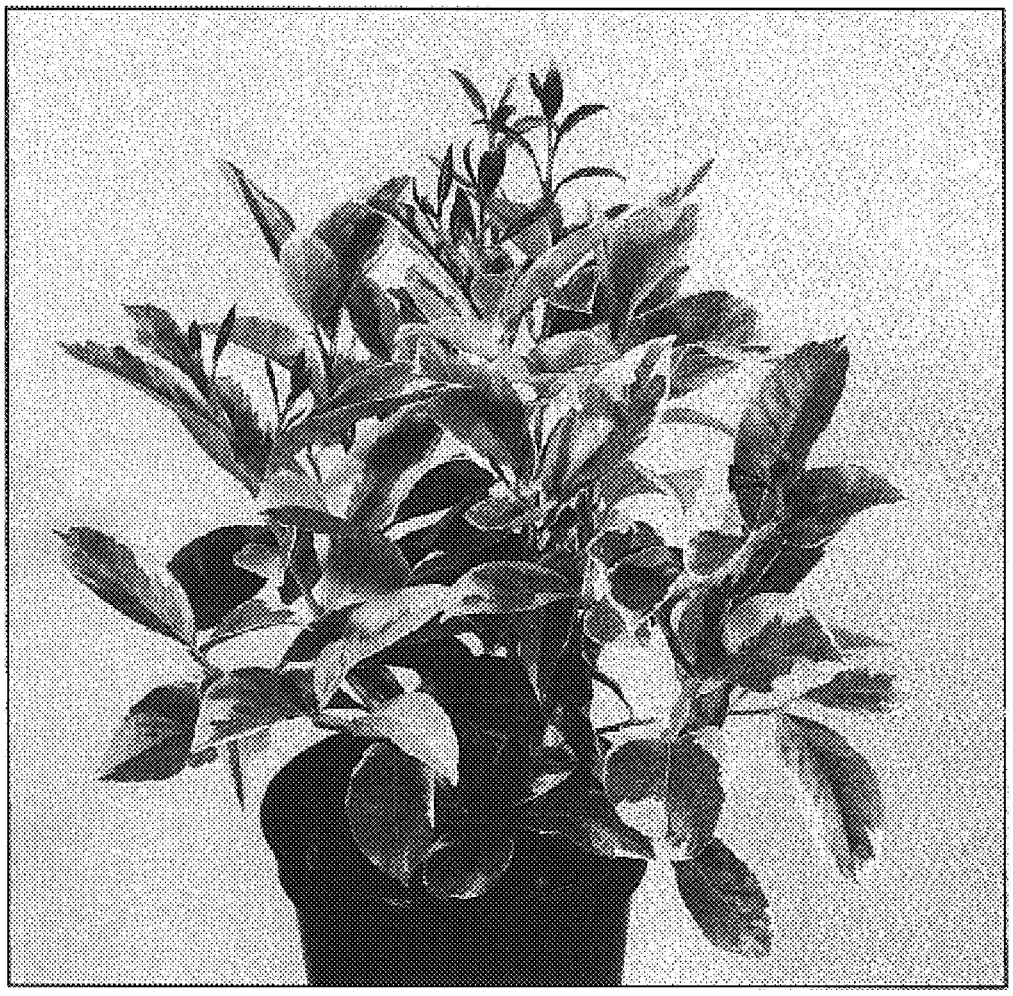

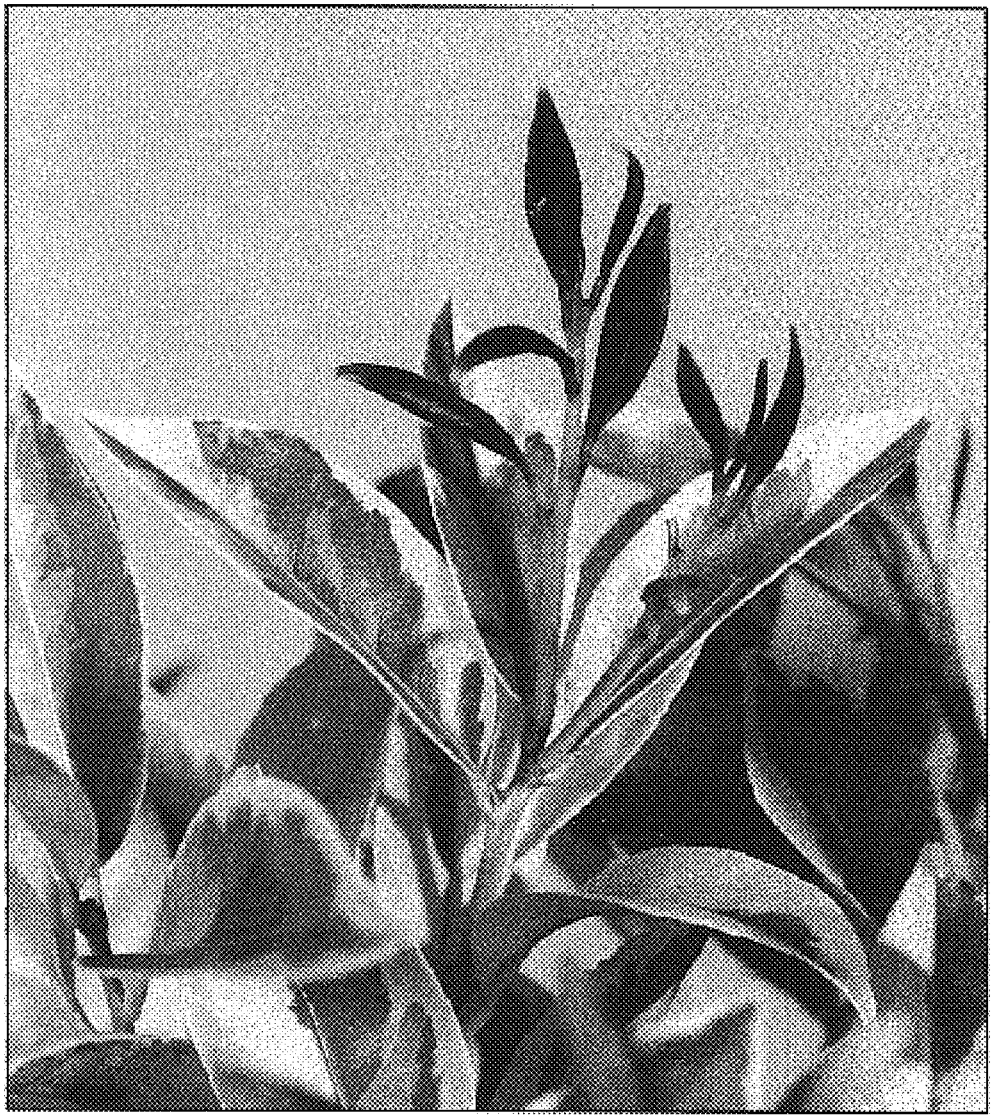
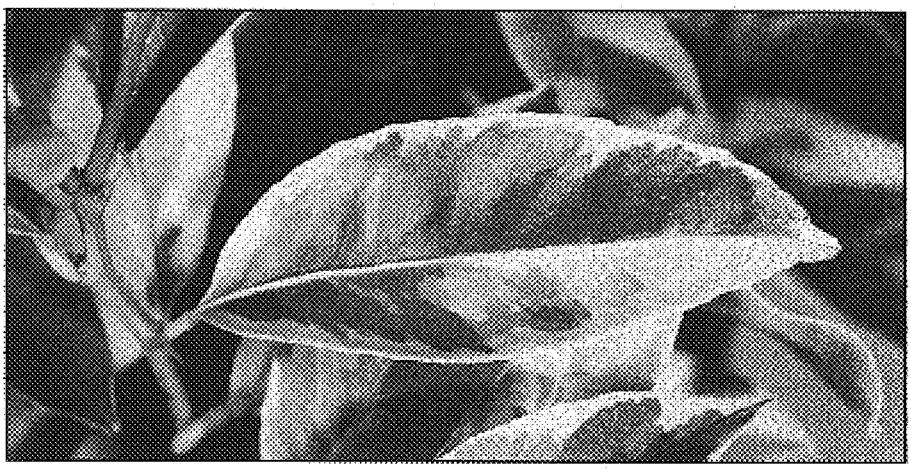

* * * * *